United States Patent [19]

Shen et al.

[11] 4,007,190
[45] Feb. 8, 1977

[54] 3,6-BIS(2-PIPERIDINYL)-2,5-PIPERAZINEDIONE COMPOUNDS

[75] Inventors: Tsung-Ying Shen, Westfield; Norman P. Jensen, Watchung; Arthur F. Wagner, Princeton, all of N.J.

[73] Assignee: Merck & Co., Inc., Rahway, N.J.

[22] Filed: June 21, 1974

[21] Appl. No.: 481,622

Related U.S. Application Data

[62] Division of Ser. No. 201,956, Nov. 24, 1971, abandoned.

[52] U.S. Cl. .............. 260/268 DK; 260/247.5 D; 260/268 PC; 424/250
[51] Int. Cl.² ...................................... C07D 401/14
[58] Field of Search ........................ 260/268 DK

[56] References Cited

UNITED STATES PATENTS 3,673,172  6/1972  Svokos et al. ............... 260/268 DK
3,718,651  2/1973  Gitterman et al. .......... 260/268 DK

OTHER PUBLICATIONS

Hanessian, et al., "Chemical Abstracts," vol. 68 (1968), col. 39968a.
Dods, et al., "Chemical Abstracts," vol. 70 (1969), col. 97202r.
Hanessian, et al., "Chemical Abstracts," vol. 71 (1969), col. 39306v.

Primary Examiner—Donald G. Daus
Assistant Examiner—James H. Turnipseed
Attorney, Agent, or Firm—David L. Rose; Walter Patton; J. Jerome Behan

[57] ABSTRACT

Novel derivatives of 3,6-bis(2-piperidinyl)-2,5-piperazinedione and processes for preparing the same. The new compounds exhibit activity in inhibiting the growth of tumors in mammals and birds, and in inhibiting the growth of certain microorganisms.

3 Claims, No Drawings

3,6-BIS(2-PIPERIDINYL)-2,5-PIPERAZINEDIONE COMPOUNDS

This is a division of application Ser. No. 201,956 filed November 24, 1971 now abandoned.

FIELD OF THE INVENTION

This invention relates to novel piperazinedione compounds. More particularly, this invention relates to a new class of substituted 3,6-bis(2-piperidinyl)-2,5-piperazinedione compounds, the acid salts thereof and processes for preparing the same.

SUMMARY OF THE INVENTION

The novel compounds of this invention can be represented by the following structural formula:

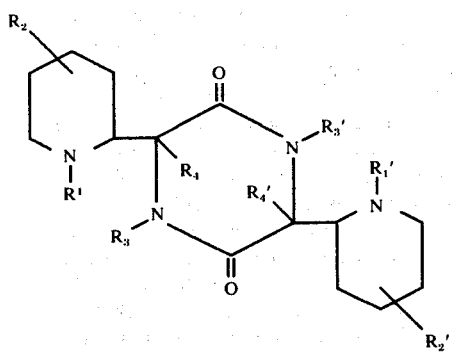

wherein $R_1$ and/or $R_1'$ represent hydrogen, loweralkyl, for example, methyl, ethyl, propyl, isopropyl, butyl, t-butyl, hexyl; substituted loweralkyl, for example, haloloweralkyl, such as 2-chloroethyl, 2-bromoethyl, dichloroethyl; loweralkylcarbonyloxyalkyl, for example acetoxymethyl, acetoxyethyl, propionoxymethyl, pivaloyloxymethyl; aroyloxyalkyl, benzoyloxymethyl, p-toloyloxy methyl; hydroxyloweralkyl, for example, 2-hydroxyethyl, 2-hydroxypropyl; aralkyl, for example, mononuclear aralkyl, benzyl, phenethyl, phenylpropyl, p-fluorobenzyl, p-chlorobenzyl, p-methoxybenzyl, p-nitrobenzyl, o-methoxybenzyl, 3,4,5-trimethoxybenzyl; acyl, for example loweralkanoyl, such as acetyl, propionyl, butyryl; haoloweralkanoyl, such as chloroacetyl, trichloroacetyl, trifluororacetyl, chloropropionyl; cycloloweralkanoyl, such as cyclopropylcarbonyl, cyclohexylcarbonyl; aroyl, such as benzoyl, p-chlorobenzoyl, toluoyl, p-fluorobenzoyl, p-nitrobenzoyl, p-phenoxybenzoyl, xyloyl; loweralkyloxycarbonyl, for example, ethoxycarbonyl, propoxycarbonyl, t-butyloxycarbonyl; haloalkyloxycarbonyl, for example $\beta,\beta,\beta$,-trichloroethoxycarbonyl; aralkyloxycarbonyl, for example benzyloxycarbonyl, p-nitrobenzyloxycarbonyl; arylthio, for example phenylsulfenyl, o-nitrophenylsulfenyl, 2,4-dinitrophenylsulfenyl; nitroso; $R_2$ and/or $R_2'$ represent halogen for example chloro, bromo, hydroxy; loweralkylsulfonyloxy, for example methyl sulfonyloxy, ethylsulfonyloxy, and the like; arylsulfonyloxy, for example, phenylsulfonyloxy; alkarylsulfonyloxy, for example p-toluenesulfonyloxy; aralkylsulfonyloxy, for example benzylsulfonyloxy; haloloweralkylsulfonyloxy, for example trifluoromethylsulfonyloxy, 2,2,2trifluoroethylsulfonyloxy; mercapto;

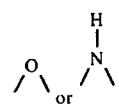

at the 4,5 or 5,6 positions; $R_3$ and/or $R_3'$ represent hydrogen, loweralkyl, for example methyl, ethyl, propyl, isopropyl, butyl, hexyl; loweralkanoyl, for example acetyl, propionyl butyryl, trifluoroacetyl, diloweralkylaminomethyl, e.g. dimethylaminomethyl, diethylaminomethyl, dipropylaminomethyl, dibutylaminomethyl, methylethylaminomethyl, methylbutylaminomethyl, cycloaminomethyl, e.g. morpholinomethyl, piperidinomethyl, nitroso; $R_4$ and/or $R_4'$ represents hydrogen, mercapto, epidithio (—S—S—);$R_1R_3$ and $R_1'R_3'$ joined together through —CH$_2$—; acid addition salts thereof wherein loweralkyl represents from 1 to 6 carbon atoms and with the proviso that when $R_2$ and $R_2'$ are chloro, $R_1$, $R_1'$, $R_3$, $R_3'$, $R_4$, and $R_4'$ are not hydrogen.

The compounds of this invention can be prepared from 3,6-bis(5-chloro-2-piperidinyl)-2,5-piperazinedione which can be prepared by fermentation. The starting material may be produced by either surface or submerged cultures, however, it is presently preferred to carry out the fermentation in the submerged state. Small scale fermentation batches may be conveniently prepared by placing suitable quantities of nutrient medium in flasks, sterilizing the flasks and contents by heating to about 120° C. for twenty minutes, inoculating the flasks with vegetative cultures of a 3,6-bis (5-chloro-2-piperidinyl)-2,5-piperazinedione producing strain of *Streptomyces griseoluteus*, loosely sealing the flasks with cotton and allowing fermentation to proceed on a shaker in a constant room at 28° C. for 3 –5 days. Larger fermentation batches may be prepared, using suitably sized tanks provided with an agitator and a means of aerating the fermentation medium. In this method the medium and tanks containing the sterilized medium is inoculated with a vegetative culture. The fermentation is allowed to proceed from 2—4 days with constant agitation or aeration of the nutrient medium at a constant temperature of about 28° C. In carrying out the fermentation according to this process it may be desirable to add a small amount of a suitable antifoaming agent. Suitable agents may include soybean oil, castor oil, 1% octadecanol in mineral oil, or a polymerized propylene glycol such as polyglycol 2,000. These agents will thus control any excess foaming that may occur in the fermentation broth during fermentation.

Aqueous media, such as those employed for the production of antibiotics, are suitable for producing 3,6-bis(5-chloro-2-piperidinyl)-2,5-piperazinedione. Such media contain sources of carbon and nitrogen assimilable by the microorganism and inorganic salts. In addition, the fermentation media contain traces of metals necessary for the growth of the microorganism which are commmonly supplied as impurities incidental to the addition of other constituents of the medium.

In general, carbohydrates such as sugars, for example, glucose, maltose, fructose, and the like, and starches such as grains, for example oats and rye, corn starch, corn meal, and the like, can be used either alone or in combination as sources of assimilable carbon in the nutrient medium. The exact quantity of the carbohydrate source or sources utilized in the medium will depend in part upon the other ingredients of the medium, but it is usually found that an amount of carbohydrate between about 1 and 6% by weight of the medium is satisfactory. These carbon sources can be used individually or several such carbon sources may be combined in the medium.

Satisfactory nitrogen sources include myriad proteinaceous materials such as various forms of hydrolysates of casein, soybean meal, corn steep liquor, distilled solubles, yeast hydrolysates, and the like. The various sources of nitrogen, either alone or in combination, are used in amounts ranging from about 0.2–6% by weight of the aqueous medium.

3,6-Bis(5-chloro-2-piperidinyl)-2,5-piperazinedione can be recovered from the broth by filtering and concentrating the filtrate under vacuum to about 1/10 the original volume and then subjecting the concentrated broths to extractive procedures.

For example, 3,6-bis(5-chloro-2-piperidinyl)-2,5-piperazinedione can be recovered from the broth or a concentrate thereof by extraction with a water immiscible solvent for the product such as butanol or chloroform. When the broth is extracted at pH 7, the free base is obtained. Alternatively, the broth can be evaporated to dryness and extracted with a suitable solvent such as a loweralkanol, for example methanol or ethanol.

Purer forms of the 3,6-bis(5-chloro-2-piperidinyl)-2,5-piperazinedione can be obtained by repeated recrystallization from hot methanol. Another procedure which can be utilized comprises absorbing the compound on anion exchange resins with polyalkylamine groups attached to a styrenedivinylbenzene polymer lattice. The absorbed antibiotics is readily eluted from the resin absorbate with water. Evaporation of the eluate to dryness affords 3,6-bis(5-chloro-2-piperidinyl)-2,5-piperazinedione which can be further purified by fractional recrystallization from methanol.

Alternatively, 3,6-bis(5-chloro-2-piperidinyl)-2,5-piperazinedione can be purified by absorption on basic alumina or silica gel and then eluted with ethylacetate or methanol.

The preferred procedure for purifying 3,6-bis(5-chloro-2-piperidinyl)-2,5-piperazinedione is as follows:

A. One part of 3,6-bis(5-chloro-2-piperidinyl)-2,5-piperazinedione is dissolved in water, filtered, and cooled in an ice bath before adjusting the pH to 7 with aqueous base. The resultant precipitate is collected and Washed first with water and then with methanol and dried at room temperature in vacuo to afford the free base dihydrate of approximately 95% purity.

B. One part of the dried material is added to methanol and warmed on a steam bath. While the solution is still warm additional methanol containing excess hydrochloride gas is added and the resulting precipitate is collected. After washing with methanol and ether the precipitate is dried at room temperature in vacuo.

C. One part of the dried material is dissolved in water and the above procedures (A) and (B) are repeated to afford a product of approximately 98% or greater purity.

D. One part of product thus obtained is warmed in methanol and the procedure from (B) to (C) is repeated again to afford an analytical sample corresponding to the formula $C_{14}H_{22}N_4Cl_2O.2HCl$.

3,6-Bis(5-chloro-2-piperidinyl)-2,5-piperazinedione is a basic substance forming acid salts. Thus, the free base, which can be extracted from the broth at pH 7 on reactions with inorganic or organic acids forms the corresponding acid salt such as the hydrochloride, sulfate, acetate, propionate, and the like.

It contains the elements carbon, hydrogen, nitrogen, oxygen and chlorine. A typical analysis of the hydrochloride salt showed it to contain 40.06% carbon, 5.79% hydrogen, 13.27% nitrogen, 8.50% oxygen, and 33.39% chlorine. This analysis indicated the molecular formula to be $C_{14}H_{22}N_4O_2Cl_2.2HCl$. The hydrochloride salt does not melt below 330° C.

When 3,6-bis(5-chloro-2-piperidinyl)-2,5-piperazinedione is reacted with acetic anhydride in the presence of pyridine at temperatures from 0° C. to room temperature, an acetylated derivative or acetate is obtained melting at 228°–229° C. with decomposition.

3,6-Bis(5-chloro-2-piperidinyl)-2,5-piperazinedione is soluble in water, lower alkanols such as methanol, ethanol, and butanol, and chloroform. The free base has low solubility in water at pH 7 but dissolves when heated. The product is soluble in aqueous acid solutions at pH 2, forming the acid salt.

The free base may be converted to a hydrochloride salt by acidifying a methanolic solution containing the free base with a lower alkanoic (preferably methanolic) solution of hydrogen chloride. 3,6-Bis(5-chloro-2-piperidinyl)-2,5-piperazinedione is stable at room temperature for 24 hours in aqueous solution at pH 2 and 10. It is labile after 3–5 minutes at 100° C. at pH 7 aqueous solution. It has been found that at 50°–60° C. the degradation proceeds slowly, some free base still being detectable after three hours. Acid hydrolysis (6N HCl 16 hours at 100° C.) leads to complete degradation.

The novel substituted 3,6-bis(2-piperidinyl)-2,5-piperazinedione compounds of this invention can be prepared by several methods. In accordance with one embodiment of this invention, novel compounds are prepared by substituting various substituents for the hydrogen atom attached to the nitrogen of the piperidinyl moieties, namely $R_1$ and $R_1'$ in structure I. Alkylation of the piperidinyl nitrogen can be accomplished by reacting an alkyl halide with the piperidinyl diketopiperazine. Among the alkylating reagents that can be employed in preparing these compounds are alkyl halides, for example methyl bromide, ethyl iodide, and propyl iodide; aralkyl halides, for example benzyl chloride, p-bromobenzylchloride, and p-nitrobenzylchloride; and acyloxyalkyl halides, for example acetoxymethyl chloride, propionoxymethyl chloride, pivaloyloxymethyl chloride, and the like. When an alkyl halide or an aralkyl halide is employed as the alkylating reagent, the reaction is run in an organic solvent, for example acetone, dimethoxyethane, dimethylformamide, and the like. When an acyloxyalkyl halide is employed as the alkylation agent, the reaction is conducted in an organic solvent such as dimethylsulfoxide, dimethylformamide, dimethoxyethane, and acetone, in the presence of a tertiary amine, for example triethylamine. The temperature for the alkylation reaction is from 0 to 50° C. depending on the nature of the alkylating agent. The alkylation can be carried out by reacting two molar equivalents of alkylating agent per mole of piperidinyl diketopiperazine, however, it is preferable to employ from 50 to 100% molar excess of alkylating agent.

The piperidinyl alkylated products may be recovered by methods known to those skilled in this art, for example, removal of solvent and purified by crystallization or chromatography.

Acyl derivatives of the piperidinyl nitrogen of the novel compounds of this invention can be prepared by reacting an acylating reagent, for example an acid halide or an acid anhydride with 3,6-bis(2-piperidinyl)-2,5-piperazinedione. Acylation with acid halides can be carried out in an organic solvent, for example acetone, dimethoxyethane, and dioxane, containing an amine, for example triethylamine, or in pyridine alone. The acid halides which can be employed in preparing the novel acyl compounds include loweralkanoyl halides, for example acetyl chloride, propionyl chloride, butyryl chloride, and the like; haloloweralkanoyl halides, for example chloroacetyl chloride, and chloropropionyl chloride; lowercycloalkanoyl halides, for example cyclopropane carboxylic acid chloride and cyclohexane carboxylic acid chloride; aroyl halides, for example benzoyl chloride, p-chlorobenzoyl chloride, p-acetamidobenzoyl chloride; alkoxy carbonyl halides, for example, ethoxycarbonyl chloride, t-butyloxycarbonyl chloride; haloalkyloxy carbonyl halides, for example $\beta\beta\beta$-trichloroethoxy carbonyl chloride; aralkyloxy carbonyl halide, for example benzyloxycarbonyl chloride, p-nitrobenzloxycarbonyl chloride, and the like. The reaction is conveniently brought about at temperatures of from between about 0° C. and 50° C., and preferably from between about 0° C. and 20° C. Generally, two moles of acid halide is employed per mole of piperidinyl diketopiperazine starting material, however, it is preferable to employ a 10–50% molar excess of acid halide for the best results.

Acylation of the piperidinyl nitrogen can also be accomplished by employing acid anhydrides, for example acetic anhydride, propionic anhydride, trifluoroacetic anhydride, glutaric anhydride. The acylation is run in an excess of the anhydride reagent, for example, from 5 to 10 moles of anhydride per mole of 3,6-bis(5-chloro-2-piperidinyl)-2,5-piperazinedione. The reaction will take place at a temperature of from 0° to the boiling point of the solvent. Isolation and purification of the acylated compounds is accomplished by methods known in the art.

The N-piperidinyl aryl thio derivatives of 3,6-bis(2-piperidinyl)-2,5-piperazinedione can be prepared by reacting phenyl sulfenyl halides with the diketopiperazine starting material. Phenylsulfenyl halides that can be employed in the process of preparing the novel derivatives include phenylsulfenyl chloride, o-nitrophenyl sulfenyl chloride, and 2,4-dinitrophenylsulfenyl chloride. The reaction is conducted in organic solvent, for example dimethyl formamide in the presence of a tertiary amine, for example triethylamine, at a temperature of from 0° to 50° C. The reaction is run with two moles or more of phenylsulfenyl compound to one mole of piperazine. The product is recovered by removing the solvent followed by solvent extraction with acetone. Purification is accomplished by chromatography.

The nitroso piperidinyl compounds of 3,6-bis(2-piperidinyl)-2,5-piperazinedione are prepared by reacting piperidinyl diketopiperazine with nitrous acid. The reaction can be run by adding sodium nitrite to an aqueous solution of the piperidinyl diketopiperazine with nitrous acid. The reaction can be run by adding sodium nitrite to an aqueous solution of the piperidinyl diketopiperazine dihydrochloride at ice bath temperatures. The reaction is allowed to stir for 24 hours at room temperature. The N-nitroso compound is recovered by filtration and purified by recrystallization.

Hydroxyloweralkyl compounds of 3,6-bis(2-piperidinyl)-2,5-piperazinedione can also be prepared by condensing an alkylene oxide, for example ethylene oxide, propylene oxide, and the like, with the piperidinyl diketopiperazine. The reaction is run in an alcoholic solvent, for example methanol, by mixing the reactants at a low temperature, for example ice-bath temperature, and then the reaction is allowed to proceed at room temperature. An excess of alkylene oxide, from 1 to 20 parts per part of piperidinyl diketopiperazine, is employed to prepare the desired compounds. The desired product is recovered by filtration and purified by recrystallization.

Haloloweralkyl compounds of 3,6-bis(2-piperidinyl)-2,5-piperazinedione can also be prepared from the corresponding hydroxyloweralkyl derivative by reaction with chloromethylenedimethylammonium chloride. The reagents are combined in dimethylformamide at a low temperature and then allowed to react at room temperature for several hours. The crude product is isolated from the reaction mixture by removal of the solvent. The residual solid is dissolved in water and the product precipitated by adjusting the pH to 7 with aqueous base. Purification is achieved by chromatography.

Also embraced by this invention are compounds in which the chlorine substituent on the piperidinyl ring of 3,6-bis(5-chloro-2-piperidinyl)-2,5-piperazinedione is replaced by other groups. Heating an aqueous solution of 3,6-bis(5-chloro-2-piperidinyl)-2,5-piperazinedione on a steam bath produces the corresponding 5-hydroxy compound. The product is recovered by neutralizing the reaction mixture with base, for example dilute sodium hydroxide, and purified by chromatography.

Reaction of a loweralkylsulfonyl halide, for example methanesulfonyl chloride, ethanesulfonyl chloride, and the like or an arylsulfonyl halide, for example benzenesulfonyl chloride, p-toluenesulfonyl chloride and the like, with an hydroxy-piperidinyl-piperazinedione in which the piperidinyl nitrogens are substituted, for example 3,6-bis[1-(o-nitrophenylsulfenyl)-5-hydroxypiperidinyl]-2,5-piperazinedione affords the corresponding 5-substituted sulfonyloxy compound. One molar equivalent of piperidinyl diketopiperazine is reacted with two molar equivalents, and preferably from 25 to 100% molar excess of sulfonyl halide in pyridine. The sulfonyl halide is added at a low temperature, for example ice-bath temperature, and the reaction is allowed to proceed to completion at room temperature. The sulfonyloxy product is recovered from the reaction mixture by removal of the solvent and purified by recrystallization from methanol.

Reaction of 3,6-bis(5-chloro-2-piperidinyl)-2,5-piperazinedione with sodium hydrogen sulfide affords the corresponding 5-mercapto-piperidinyl compound. Formation of the mercapto compound can be accomplished by reacting one molar equivalent of the starting piperidinyl diketopiperazine compound with two molar equivalents, and preferably an excess of from 100 to 500% by weight of sodium hydrogen sulfide. The reaction is run in an alcoholic solvent, for example ethanol, at a temperature of from 20° C. to the boiling point of the solvent. The desired 5-mercapto substituted piperidinyl diketopiperazine product is readily recovered from the reaction mixture by removal of the solvent and purified by chromatography.

The chlorine substituent of 3,6-bis(5-chloro-2-piperidinyl)-2,5-piperazinedione can also be replaced by a bromine atom by treatment with sodium bromide in dimethylsulfoxide. One mole of piperidinyl diketopiperazine is reacted with an excess, for example 10–50% molar excess, of sodium bromide at 35%. Removal of the solvent and purification by chromatography affords 3,6-bis(5-bromo-2-piperidinyl)-2,5-piperazinedione which can be isolated as the dihydrochloride on treatment with methanol containing hydrogen chloride.

The novel dehydropiperidinyl compounds of this invention are prepared by reacting 3,6-bis-[1-trifluoroacetyl-5-(p-toluenesulfonyloxy)-2-piperidinyl]-1,4-bis-trifluoroacetyl-2,5-piperazinedione with potassium tertiary butoxide in dimethylsulfoxide. Approximately 10 moles of alkoxide is employed per mole of piperidinyl-diketopiperazine starting material and the reaction is heated at 70° C. for several hours. After the solvent is removed, water is added to the residue. The product which consists of a mixture of 3,6-bis-($\Delta$4 and $\Delta$5-2-dehydropiperidinyl)-2,5-piperazinediones is recovered by filtration and purified by chromatography on silica gel.

Epoxidation of the mixture of dehydropiperidinyl compounds of this invention affords a mixture of 3,6-bis(4,5 and 5,6-epoxy-2-piperidinyl)-2,5-piperazinediones. Reaction of the starting dehydropiperidinylcompound with a perorganic acid such as peracetic, perbenzoic or m-chloroperbenzoic acid, is conveniently brought about at temperatures of between about 0° C. and 30° C. This peroxidation is preferably carried out in an inert hydrocarbon solvent such as chloroform, methylene dichloride, benzene, toluene, and the like. The reaction time is not critical, and it is preferable to continue the peroxidation until the maximum amount of epoxide has been produced. Generally, an excess of organic peracid is utilized for best results. The desired products may be recovered by methods known to those skilled in this art, for instance by decomposition of excess perorganic acid and removal of the solvent.

The 3,6-{4-(3,7-diaza [4,1,0]heptyl)} and 3,6-{3-(2,7-diaza [4,1,0]heptyl)}-2,5-piperazinedione compounds of this invention are conveniently prepared by the reaction of iodine isocyanate, prepared from silver cyanate and iodine, with a dehydropiperidinyl diketopiperazine compound. The intermediate iodo-isocyanate addition compound is refluxed with methanol to form the iodo-carbmethoxyamino intermediate, which is refluxed with base, for example aqueous potassium hydroxide to produce the aziridinyl compound. The formation of iodine-isocyanate and its reaction with the dehydropiperidinyl diketopieprazine is run in dimethoxyethane. The reagents are combined at a low temperature, for example ice-bath temperature, and then the reaction is allowed to run to completion at room temperature. The reaction product is filtered and washed with methanol. The filtrate and washings are concentrated in vacuo and the residue refluxed with methanol. After addition of aqueous base, the mixture is refluxed for several hours. The desired product is recovered by removal of the solvent and purified by chromatography on Fouorosil.

Pursuant to another embodiment of this invention, novel compounds of 3,6-bis-(2-piperidinyl)-2,5-piperazinedione are prepared by replacing various groups for the hydrogen atom attached to the nitrogen of the piperazinedione moiety, that is, $R_3$ and $R_3'$ in structure I. In order to prepare the compounds wherein $R_3$ and $R_3'$ are other than hydrogen, it is first necessary to block or protect the piperidinyl nitrogen substituents at $R_1$ and $R_1'$. The piperidinyl nitrogens can be blocked by alkylating or acylating with any of the reagents mentioned above for preparing compounds having substituents at $R_1$ and $R_1'$. Alkylation of a compound wherein $R_1$ and $R_1'$ is an acyl radical can be carried out in dimethylformamide with an alkylhalide, for example methyl iodide, in the presence of sodium hydride. Under these reaction conditions, alkylation of the piperazinedione nitrogens is followed by removal of the acyl blocking groups on the piperidinyl nitrogen atoms during work up. An excess of reagents, for example three moles of alkylating agent and two moles of sodium hydride, are employed per mole of diketopiperazine. After the reaction is completed, the solvent is removed and the residue is triturated with dilute base, such as sodium hydroxide. The 1,4-alkylated-3,6-bis-(2-piperidinyl)-2,5-piperazinedione is isolated and purified by chromatography.

The novel 3,6-bis-(2-piperidinyl)-2,5-piperazinedione compounds wherein $R_1$, $R_1'$, $R_3$, and $R_3'$ are acyl radicals can be prepared by reacting a large excess of an acyl anhydride, for example ten moles per mole of piperazinedione starting material. The reaction is run in the presence of an acid, for example the acid from which the anhydride is derived, by refluxing for several hours. The 3,6-bis-(1-acylated-2-piperidinyl)-1,4-bis-acylated-2,5-piperazinedione compound are isolated by removing any volatiles and triturating with an alcohol, for example methanol.

The novel compounds of this invention wherein $R_3$ and $R_3'$ represent a dialkylaminomethyl radical can be prepared by reacting a secondary amine, for example diethylamine, morpholine and the like, and formaldehyde with a piperidinyl diketopiperazine in which the piperidinyl nitrogens are substituted with a protecting group such as a loweralkyl radical. The reaction is conveniently run in an alcoholic solvent, such as ethanol, at reflux. Although two molar equivalents of formaldehyde and a secondary amine per mole of diketopiperazine may be utilized in the process, it is preferable to run the reaction with from 5–50% molar excess of formaldehyde and amine. The novel compounds are recovered by procedures well known in the art, for example filtration and purification which can be accomplished by crystallization or chromatography.

Preparation of compounds wherein $R_3$ and $R_3'$ are nitroso can be accomplished by reacting a piperidinyl diketopiperazine which has the piperidinyl nitrogens substituted with a protecting group such as a loweralkyl radical or acyl radical, with a nitrosylating agent such as nitrosyl sulfuric acid. The reaction is conveniently run by adding the nitrosylating agent to the piperidinyl diketopiperazine, for example 3,6-bis(1-methyl-5-chloro-2-piperidinyl)- or 3,6-bis(1-trifluoroacetyl-5-chloro-2-piperidinyl)-2,5-piperazinedione in a mixture of acetic acid and acetic anhydride containing excess sodium acetate or potassium acetate. Although the reaction can be carried out by reacting two molar equivalents of nitrosylating reagent per molar equivalent of piperidinyl diketopiperazine, it is preferable to employ from 10 to 50% molar excess of nitrosylating agent. The nitrosylating agent is added at a temperature of from 0° C. to 20° C. and the reaction is allowed to stir for 15 hours at 20° C. The substituted 1,4-dinitroso piperidinyl diketopiperazine is isolated by removing the volatile components in vacuo and suspending the residue in water and adjusting the pH to 7 with aqueous base, for example sodium hydroxide. Purification is accomplished by chromatography on silica gel.

When 1,4-dinitroso-3,6-bis(1-trifluoroacetyl-5-chloro-2-piperidinyl)-2,5-piperazinedione is treated with dilute base, the trifluoroacetyl groups can be removed to afford 1,4-dinitroso-3,6-bis(5-chloro-2-piperidinyl)-2,5-piperazinedione. The reaction is conducted by adding the piperidinyl diketopiperazine to a two phase system of chloroform and aqueous dilute base, for example 2N sodium hydroxide. The addition and reaction are carried out at 0° C. The product is isolated by removing the solvents in vacuo and purification is by chromatography on silica gel.

Dehydrohalogenation of 3,6-bis(5-chloro-2-piperidinyl)-2,5-piperazinedione with a strong organic base, for example 1,5-diazobicyclo-[5,4,0]undec-5-ene, affords 3,6-bis-{2-[1-azabicyclo (3,1,0)-hexane]}-2,5-piperazinedione. The reaction is run by heating the reagents at 95° C. with stirring for 10 minutes and then heating on a steam bath for 20 minutes. The mixture is boiled with methanol and after cooling, ether is added to the reaction mixture. After standing several hours, the dehydrohalogenation precipitates out and the product is isolated by filtration and purified by crystallization from methanol.

The preparation of the novel compounds of this invention wherein the piperidinyl and diketopiperazine nitrogen atoms are joined through a methylene bridging group can be prepared by reacting the 3,6-bis(2-piperidinyl)-2,5-piperazinedione starting compound with formaldehyde in formic acid. The reaction is carried out by dissolving the piperidinyl diketopiperazine compound in formic acid and adding formaldehyde with stirring. The reaction is allowed to stand for one hour and the desired product, 3,11-dichloro-8,16-dioxo (2,3c:5,6C') bis- octahydro [imidazo (1,5a)-pyridino] hexahydropyrazine, isolated by filtration.

The novel compounds of this invention wherein the 3,6 positions of the diketopiperazine are joined by a epidithio (—S—S—) linkage are prepared by first reacting a completely protected piperidinyl diketopiperazine, for example 1,4-dimethyl-3,6-bis(1-trifluoroacetyl-5-chloro-2-piperidinyl)-2,5-piperazinedione, with phosphorous pentabromide in an organic solvent, such as o-dichlorobenzene. The reaction is run in an excess of phosphorus pentabromide, for example 3 moles to 1 mole of diketopiperazine, at 150° C. After cooling the reaction, petroleum ether is added and the intermediate bromo compound precipitates and is collected. This intermediate is reacted with a molar equivalent of sodium tetrasulfide by refluxing for 5 hours in an alcohol, such as anhydrous ethanol. The product can be isolated from the reaction mixture by filtering to remove any solids and concentrating the solution in vacuo. The remaining residue is purified by chromatography on silica gel. Treatment of the purified material with base, for example dilute ammonium hydroxide, affords the 3,6-epidithia-3,6-bis(5-chloro-2-piperidinyl)-1,4-dimethyl-2,5-piperazinedione. The dihydrochloride can be prepared by treating the material purified by chromatography on silica gel with methanol containing excess hydrogen chloride.

The compounds of this invention wherein $R_4$ and $R_4'$ are mercapto (—SH) can be prepared from the corresponding 3,6-epidithia piperidinyl diketopiperazine, for example, 3,6-epidithia-3,6-bis(5-chloro-2-piperidinyl)-1,4-dimethyl-2,5-piperazinedione by reaction with sodium borohydride. The reaction is conveniently brought about by adding two moles of sodium borohydride to one mole of the epidithia compound in an alcoholic solvent, for example methanol. The addition is made at a low temperature, ice-bath temperature, and the reaction mixture is refluxed for 1 hour. After the solvent is removed, the residue is treated with aqueous base, for example dilute ammonium hydroxide. The dimercapto compound is isolated by methods known in the art, e.g. filtration and further purified by chromatography on silica gel. The dihydrochloride can be prepared by stirring the free base in methanol containing excess hydrogen chloride.

Also included within the scope of this invention are the acid addition salts of the compounds of this invention formed from such acids as hydrochloric acid, hydrobromic acid, phosphoric acid, acetic acid, ascorbic acid, tartaric acid, maleic acid, and the like.

The hydrochloride salts of the novel compounds of this invention can be prepared by acidifying a methanolic solution containing the free base of the compound with hydrogen chloride.

The following examples illustrate methods of preparing the novel compounds of the present invention. It is to be understood, however, that they are given for the purposes of illustration and not of limitation.

EXAMPLE 1

3,6 Bis-(5-hydroxy-2piperidinyl)-2,5-Piperazinedione 1.0 G. of 3,6-bis(5-chloro-2-piperidinyl)-2,5-piperazinedione is heated in 50 ml. of water for ½ hour on a steam bath. The solution is filtered, neutralized with dilute sodium hydroxide and freeze-dried to a white solid weighing 1.16 g. Purification of 300 mg. is accomplished by chromatography on 6 × 1000 μ on silica gel plate using 5:1:2 n-butanol:acetic acid:water as an eluant to give 165 mg. which is dissolved in 15 ml. of hot methanol. Filter solution and bubble in hydrogen chloride gas. Collect precipitate and wash 2 × 5 ml. with methanol and 20 ml. of ether to give 80 mg. of 3,6-bis-(5-hydroxy-2-piperidinyl)-2,5-piperazinedione dihydrochloride.

EXAMPLE 2

3,6-Bis-[1-(o-nitrophenylsulfenyl)-5-chloro-2-piperidinyl]-2,5-Piperazinedione

A 152 mg. portion of 3,6-bis(5-chloro-2-piperidinyl)-2,5-piperazinedione is stirred in 3 ml. of dry dimethylformamide and 165 mg. of o-nitrosulfenylchloride and 0.12 ml. of triethylamine are added. After stirring 1 hour, 5 ml. of chloroform is added. After 2 hours more stirring, the chloroform is removed in vacuo and the residue filtered before addition of 3 ml. each of chloroform and dimethylformamide. After addition of 0.070 ml. of triethylamine and 90 mg. of o-nitrophenylsulfenyl chloride, the mixture is stirred for 15 hours. The solvents are then removed in vacuo and the solid residue is extracted with 15 ml. of acetone. The acetone extract is concentrated to a solid and extracted with acetone. This process is continued until material is obtained which is completely soluble in 15 ml. of acetone. The acetone-soluble material is then chromatographed on silica gel plates. The main band yields 180 mg. of product, m.p. about 170°–180° C. Recrystallization from methanol yields an analytical sample, m.p. 177°–179° C., as a methanol solvate.

When 3,6-bis (5-hydroxy-2-piperidinyl)-2,5-piperazinedione is employed in place of 3,6-bis (5-chloro-2-piperidinyl)-2,5-piperazinedione, there is obtained 3,6-bis [1-(o-nitrophenylsulfenyl)-5-hydroxy-2-piperidinyl]-2,5-piperazinedione.

EXAMPLE 3

3,6-Bis-[1-(o-nitrophenylsulfenyl-5-methylsulfonyloxy-2-piperidinyl]-2,5-piperazinedione A pyridine solution of one mole of 3,6-bis-[1-(o-nitrophenylsulfenyl)-5-hydroxy-2-piperidinyl]-2,5-piperazinedione is cooled and 2.5 moles of methanesulfonyl chloride is added. After standing 24 hours, the pyridine is removed in vacuo and the residue is washed with water before recrystallization from methanol.

EXAMPLE 4

3,6-Bis-[5-methylsulfonyloxy-2-piperidinyl]-2,5-piperazinedione Dihydrochloride

To a mixture of 3,6-bis-[1-(o-nitrophenyl-sulfenyl)-5-methylsulfonyloxy-2-piperidinyl]-2,5-piperazinedione in 50-fold methanol is added methanol containing excess hydrogen chloride gas. After stirring 12 hours, the mixture is warmed briefly. After cooling, the precipitate is collected and purified by chromatography.

EXAMPLE 5

3,6-Bis-(1-chloroacetyl-5-chloro-2-piperidinyl)-2,5-Piperazinedione

A mixture of 1 mole of 3,6-bis(5-chloro-2-piperidinyl)-2,5-piperazinedione and 100 parts of dry pyridine is stirred and 3.0 moles of chloroacetylchloride is slowly added with ice-bath cooling. After stirring one day at room temperature, the mixture is warmed briefly on a steam bath and the solvent is removed in vacuo. Crystallization of the residue from methanol gives 3,6-bis-(1-chloroacetyl-5-chloro-2-piperidinyl) 2,5-piperazinedione.

In an analogous manner beginning with 3-chloropropionyl chloride, butyryl chloride, cyclopropanecarboxylic acid chloride, cyclohexanecarboxylic acid chloride, nicotinoyl chloride-hydrochloride, p-chlorobenzoyl chloride, and phthaloylglycyl chloride in place of chloroacetyl chloride, the corresponding acylated piperidinyl compounds are prepared 3,6-bis [1 (3-chloropropionyl)-5-chloro-2-piperidinyl]-2,5-piperazinedione, 3,6-bis (1-butyryl-5-chloro-2-piperidinyl)-2,5-piperazinedione, 3,6bis (cyclopropylcarbonyl-5-chloro-2-piperidinyl)-2,5-piperazinedione, 3,6-bis (1-cyclohexylcarbonyl-5-chloro-2-piperidinyl)-2,5-piperazinedione, 3,6-bis(1-nicotinoyl-5-chloro-2-piperidinyl)-2,5-piperazinedione, 3,6-bis (1-p-chlorobenzoyl-5-chloro-2-piperidinyl)-2,5-piperazinedione, and 3,6-bis (1-phthaloylglycyl-5-chloro-2-piperidinyl)-2,5-piperazinedione.

EXAMPLE 6

3,6-Bis-(1-glycyl-5-chloro-2-piperidinyl)-2,5-Piperazinedione

One mole of 2,6-bis-(1-phthaloylglycyl-5-chloro-2-piperidinyl)-2,5-piperazinedione and 5-6moles of hydrazine hydrate are refluxed in 200 parts of ethanol for 5 hours. The solvent is removed in vacuo and the residue is washed with small amounts of water before being purified by chromatography on silica gel.

EXAMPLE 7

3,6-[1-tetrahydro-2H-1,3,2-oxazaphosphorin-2-yl)-5-chloro-2-piperidinyl]-2,5-piperazinedione A mixture of one mole of 3,6-bis(5-chloro-2-piperidinyl)-2,5-piperazinedione and 1.5 moles of triethylamine is stirred in 200 parts of acetone and 2.2 moles of 2-chloro-tetrahydro-2H-1,3,2-oxazaphosphorine p-oxide is added slowly in 10 parts of methylene chloride. After stirring 5 hours at room temperature and 24 hours at reflux, the solvents are removed in vacuo and the residue is washed with small amounts of dilute hydrochloric acid followed by water. The residue is then purified by chromatography on silica gel to afford 3,6-[1-(tetrahydro 2H-1,3,2-oxazaphosphorin-2-yl)-5-chloro-2-piperidinyl]2,5-piperazinedione.

EXAMPLE 8

3,6-Bis-(5-mercapto-2-piperidinyl)-2,5-Piperazinedione

One mole of 3,6-bis(5-chloro-2-piperidinyl)-2,5-piperazinedione is added to 2.2 moles of sodium hydrogen sulfide in 50 parts of ethanol. The mixture is stirred one day at room temperature and then refluxed 15 hours. The solvent is removed in vacuo and the residue purified by chromatography on silica gel to afford 3,6-bis-(5-mercapto-2-piperidinyl)-2,5-piperazinedione.

EXAMPLE 9

3,6-Bis-(1-methyl-5-chloro-2-piperidinyl)-2,5-Piperazinedione

A 1.0 g. portion of 3,6-bis(5-chloro-2-piperidinyl)-2,5-piperazinedione is stirred in 150 ml. of acetone and 8 ml. of methyl bromide for 4 days. The mixture is concentrated in vacuo to a solid which is stirred for an additional 5 days in 125 ml. of acetone and 10 ml. of methyl bromide. After concentration in vacuo the residue is dissolved in 25 ml. of dilute hydrochloric acid and filtered. The pH is then adjusted to 7.1 with 1N sodium hydroxide and .88 g. of solid is collected; extraction with 3 × 10 ml. of 10% methanol/chloroform gives .35 g. of solid material. Chromatography on 4 × 1000 μ silica gel plates (10% methanol/chloroform) gives 175 mg. of product which is slurried in 20 ml. of 1:5 methanol: chloroform and is heated with gaseous hydrogen chloride. After adding 5 ml. of ether, 141 mg. of the dihydrochloride of 3,6-bis-(1-methyl-5-chloro-2-piperidinyl)-2,5-piperazinedione is collected.

EXAMPLE 10

3,6-Bis-(1-benzyl-5-chloro-2-piperidinyl)-2,5-Piperazinedione

One mole of 3,6-bis(5-chloro-2piperidinyl)-2,5-piperazinedione is stirred in 150 parts of acetone and 2.2 moles of benzyl bromide is added. The mixture is stirred 24 hours and refluxed 24 hours. The solvent is removed in vacuo and treated as in the preparation of 3,6-bis-(1-methyl-5-chloro-2-piperidinyl)-2,5-piperazinedone.

EXAMPLE 11

3,6-Bis-(5-bromo-2-piperidinyl)-2,5-Piperazinedione Dihydrochloride

One mole of 3,6-bis-[1-(o-nitrophenylsulfenyl)-5-methylsulfonyloxy-2-piperidinyl]-2,5-piperazinedione is stirred in 10 parts of dimethylsulfoxide with 2.2 moles of sodium bromide for 2 weeks at 35°. The insolubles are removed by filtration, and the filtrate is concentrated in vacuo to a gum which is purified by chromatography on silica gel. The purified material is then treated with methanol containing excess hydrogen chloride gas as described in the preparation of 3,6-bis-[5-methylsulfenyloxy-2-piperidinyl]-2,5-piperazinedione dihydrochloride.

EXAMPLE 12

3,6-Bis-(1-pivaloyloxymethyl-5-chloro-2-piperidinyl)-2,5-Piperazinedione

One mole of 3,6-bis(5-chloro-2-piperidinyl)-2,5-piperazinedione is stirred in 10 parts of dry dimethylsulfoxide with 3 moles of triethylamine and 3 moles of pivaloyloxymethyl chloride is added. After stirring one week the solvent is removed in vacuo and purification is achieved by chromatography on silica gel.

EXAMPLE 13

1,2-Bis-(N-morpholinomethyl)-3,6-Bis-(1-methyl-5-chloro-2-piperidinyl)-2,5-Piperazinedione One mole of 3,6-bis-(1-methyl-5-chloro-2-piperidinyl)-2,5-piperazinedione, 2.1 moles of formalin and 2.1 moles of morpholine are refluxed in 5 parts of ethanol for 15 minutes. After cooling the product is collected and purified by recrystallization from methanol.

EXAMPLE 14

3,6-Bis-[1-trifluoroacetyl-5-(p-toluenesulfonyloxy)-2-Piperidinyl]-1,4-Bis-Trifluoroacetyl-2,5-Piperazinedione One mole of 3,6-bis-[5-(p-toluenesulfonyloxy-2-piperidinyl]-2,5-piperazinedione prepared from 3,6-bis-[1-(o-nitrophenylsulfenyl)-5-hydroxy-2-piperidinyl]-2,5-piperazinedione according to the procedure of Example 4 is refluxed with 10 moles of trifluoroacetic anhydride and 5 moles of trifluoroacetic acid for 15 hours. The excess solvent and reagent are removed in vacuo and the residue triturated with methanol to afford the desired product.

EXAMPLE 15

Mixture of 3,6-Bis-[Δ4 and Δ5-2-dehydropiperidinyl]-2,5-Piperazinediones

One mole of 3,6-bis-[1-trifluoroacetyl-5-(p-toluenesulfonyloxy)-2-piperidinyl]-1,4-bis-trifluoroacetyl-2,5-piperazinedione is dissolved in 20 parts of dry (distilled from barium oxide) dimethylsulfoxide and 10 moles of freshyl prepared potassium tertiary butoxide is added. The mixture is stirred at 70° for 2 hours, and the solvent is removed in vacuo. Water is cautiously added to the residue and after stirring one hour at room temperature, the solid is collected and the olefin fraction purified by chromatography on silica gel.

EXAMPLE 16

Mixture of 3,6-Bis-(Δ4 and Δ5-2-dehydro-1-trifluoroacetyl-2-piperidinyl)-1,4-Bis-Trifluoroacetyl-2,5-Piperazinediones One mole of 3,6-bis-[Δ4 and Δ5-2-dehydropiperidinyl]-2,5-piperazinedione is refluxed 10 hours with 10 moles of trifluoroacetic anhydride and 2 moles of trifluoroacetic acid. The volatiles are removed in vacuo and the residue triturated with methanol to afford a mixture of 3,6-bis-(Δ4 and Δ5-2-dehydro-1-trifluoroacetyl-2-piperidinyl)-1,4-bis-trifluoroacetyl-2,5-piperazinediones.

EXAMPLE 17

Mixture of 3,6-bis-(4,5- and 5,6-epoxy-2-piperidinyl)-2,5-Piperazinediones

One mole of 3,6-bis-(Δ4 and Δ5-2-dehydro-1-trifluoroacetyl-2-piperidinyl)-1,4-bis-trifluoroacetyl-2,5-piperazinediones is stirred in 200 parts of chloroform with 5.0 moles of m-chloroperbenzoic acid for two weeks. The chloroform is removed in vacuo and the residue is stirred with excess dilute base and the insolubles are collected. Purification by chromatography on Florosil produces a mixture of 3,6-bis-(4,5- and 5,6-epoxy-2-piperidinyl)-2,5-piperazinedione.

EXAMPLE 18

Mixture of 3,6-[4-(3,7 diaza [4,1,0]heptyl]and 3,6-[3-(2,7-diaza [4,1,0]heptyl] 2,5-Piperazinedione To a stirred mixture of 2.2 mmoles of iodine and 3.0 mmoles of silver cyanate are stirred in 10 ml. of dry dimethoxyethane with ice-bath cooling and 1.0 mmole of a mixture of 3,6-bis (Δ4 and Δ5-2-dehydropiperidinyl)-2,5-piperazinedione is added. After stirring 1 hour at 0° and 1 week at room temperature, the mixture is filtered through celite. The collected solid is then washed well with dry methanol. The filtrate and washings are concentrated in vacuo and the residue stirred and refluxed for 12 hours in 25 ml. of dry methanol. 2.0 Mmoles of 10% potassium hydroxide is added and the mixture is refluxed 3 hours more. The solvent is then removed in vacuo and the residue is washed with water and purified by chromatography on Fluorosil.

EXAMPLE 19

3,6-Bis-(1-trifluoroacetyl-5-chloro-2-piperidinyl)-1,4-Bis-Trifluoroacetyl-2,5-Piperazinedione One mole of 3,6-bis(5-chloro-2-piperidinyl)-2,5-piperazinedione is stirred 12 hours with 10 moles of trifluoroacetic anhydride and 5 moles of trifluoroacetic acid. The mixture is then refluxed 15 hours and the volatiles are removed in vacuo. The residue is triturated with methanol.

EXAMPLE 20

3,11-Dichloro-8,16-Dioxo(2,3C:5,6,C')Bis-{Octahydro[imidazo(1,5a)Pyridino]} Hexahydropyrazine One mole of 3,6-bis(5-chloro-2-piperidinyl)-2,5-piperazinedione is dissolved in one part of 95–100% formic acid and 0.7 parts of 37% formaldehyde is added with stirring. After standing one hour, the insoluble material is collected by filtration and washed with ether to afford 3,11-dichloro-8,16-dioxo(2,3C:5,6,C')bis {octahydro [imidazo (1,5a)pyridino} hexahydropyrazine

EXAMPLE 21

3,6-Bis(1-methyl-1-oxo-5-chloro-2-piperidinyl)-2,5-Piperazinedione

One mole of 3,6-bis-(1-methyl-5-chloro-2-piperidinyl)-2,5-piperazinedione is stirred in 200 ml. methanol and the mixture is cooled with an ice bath before 2 moles of 30% hydrogen peroxide is added dropwise. After stirring 2 hours at room temperature, another 2 moles of 30% hydrogen peroxide are added and after 15 hours stirring, another 2 moles of hydrogen peroxide are added. After stirring 15 hours, excess peroxide is decomposed with platinum black. The mixture is filtered and concentrated in vacuo to a residue which is purified by chromatography on Florosil.

EXAMPLE 22
3,6-Bis(1-benzyl-1-oxo-5-chloro-2-piperidinyl)-2,5-Piperazinedione One mole of 3,6-bis-(1-benzyl-5-chloro-2-piperidinyl)-2,5-piperazinedione is stirred in 200 ml. methanol and the mixture is cooled with an ice bath before 2 moles of 30% hydrogen peroxide is added dropwise. After stirring 2 hours at room temperature, another 2 moles of 30% hydrogen peroxide are added and after 51 hours stirring, another 2 moles of hydrogen peroxide are added. After stirring 15 hours, excess peroxide is decomposed with platinum black. The mixture is filtered and concentrated in vacuo to a residue which is purified by chromatography on Florosil.

EXAMPLE 23
3,6-Bis[1-($\beta\beta\beta$-trichloroethoxycarbonyl)-5-Chloro-2-Piperidinyl]-2,5-Piperazinedione One mole of 3,6-bis(5-chloro-2-piperidinyl)-2,5-piperazinedione is stirred in 200 parts of acetone with 3 moles of triethylamine and 3 moles of $\beta\beta\beta$-trichloroethoxycarbonyl chloride in 100 parts of acetone are added dropwise with stirring over a period of one hour. The mixture is stirred one day and the volatiles are removed in vacuo and the residue washed with water before purification by chromatography on silica gel.

When propoxycarbonyl chloride and benzyloxycarbonyl chloride are employed in place of $\beta\beta\beta$-trichloroethoxycarbonyl chloride in the above procedure, 3,6-bis (1-propoxycarbonyl-5-chloro-2-piperidinyl)-2,5-piperazinedione and 3,6-bis (1-benzyloxycarbonyl-5-chloro-2-piperidinyl)-2,5-piperazinedione are obtained.

EXAMPLE 24
3,6-Bis(1-trifluoroacetyl-5-chloro-2-piperidinyl)-2,5-Piperazinedione One mole of 3,6-bis(5-chloro-2-piperidinyl)-2,5-piperazinedione is stirred in 100 parts of pyridine and 5 moles of trifluoroacetic anhydride are added. After stirring 15 hours, the volatiles are removed in vacuo and the residue is crystallized from methanol.

EXAMPLE 25
1,4-Dimethyl-3,6-Bis-(5-chloro-2-piperidinyl)-2,5-Piperazinedione One mole of 3,6-bis(1-trifluoroacetyl-5-chloro-2-piperidinyl)-2,5-piperazinedione is dissolved in 50 parts of dry dimethylformamide. The solution is stirred under a nitrogen atmosphere and 2 moles of sodium hydride are added. After stirring 5 hours, 3 moles of methyliodide are added. The mixture is stirred 15 hours and the solvent is removed in vacuo. The residue is triturated with dilute sodium hydroxide, stirred in dilute sodium hydroxide for one hour, and the solid is collected and purified by chromatography on silica gel to afford 1,4-dimethyl-3,6-bis-(5-chloro-2-piperidinyl)-2,5-piperazinedione.

EXAMPLE 26
1,4-Dimethyl-3,6-Bis(1-trifluoroacetyl-5-chloro-2-piperidinyl)-2,5-Piperazinedione One mole of 1,4-dimethyl-3,6-bis(5-chloro-2-piperidinyl)-2,5-piperazinedione is stirred in 100 parts of pyridine and 5 moles of trifluoroacetic anhydride are added. After stirring 15 hours, the volatiles are removed in vacuo and the residue is crystallized from methanol.

EXAMPLE 27
3,6-Epidithia-3,6-Bis-(5-chloro-2-piperidinyl)-1,4-Dimethyl-2,5-Piperazinedione Dihydrochloride One mole of 1,4-dimethyl-3,6-bis(1-trifluoroacetyl-5-chloro-2-piperidinyl)-2,5-piperazinedione is stirred in 15 parts of o-dichlorobenzene with 3 moles of phosphorous pentabromide. The mixture is heated to 150° for 15 minutes, cooled and diluted with petroleum ether. The precipitate is collected, dried in vacuo and refluxed 5 hours with an equivalent of sodium tetrasulfide in 20 parts of anhydrous ethanol. The mixture is then filtered and the filtrate concentrated in vacuo to a residue which is purified by chromatography on silica gel. The purified material is then stirred in excess dilute ammonium hydroxide and collected on a filter. The dihydrochloride is prepared by stirring in methanol containing excess hydrogen chloride after the free base has been purified by chromatography on silica gel.

EXAMPLE 28
3,6-Dimercapto-3,6-Bis-(5-chloro-2-piperidinyl)-1,4-Dimethyl-2,5-Piperazinedione Dihydrochloride To one mole of 3,6-epidithia-3,6-bis-(5-chloro-2-piperidinyl)-1,4-dimethyl-2,5-piperazinedione in 25 parts of methanol is added portionwise, with stirring, and ice bath cooling, 2.0 moles of sodium borohydride. After stirring one hour at room temperature the mixture is refluxed one hour. The solvent is removed in vacuo and the residue is stirred with 20 parts of water and excess dilute ammonium hydroxide. The solid is then collected on a filter and purified by chromatography on silica gel. The dihydrochloride is prepared by stirring in methanol with excess hydrogen chloride.

EXAMPLE 29
3,6-Bis-{2-[1-azabicyclo(3,1,0)-hexane]} 2,5-Piperazinedione

A 1.50 g. portion of finely ground 3,6-bis(5-chloro-2-piperidinyl)-2,5piperazinedone is mixed with 2.25 ml. of 1,5-diazobicyclo[5,4,0]undec-5-ene and heated in an oil bath at 95° C., with stirring, for 10 minutes. The mixture is then stirred and heated on a steam bath for 20 minutes. A 25 ml. portion of methanol is added and the mixture is brought to a boil. After cooling, 10 ml. of ether is added and the mixture is allowed to stand 15 hours. Collect 0.54 g. Let stand and collect .14 g. more. Recrystallize both crops from methanol to give .47 g. of 3,6-bis-{2-[1-azabicyclo(3,1,0)-hexane]}-2,5-piperazinedione.

EXAMPLE 30
3,6-Bis-(N-nitroso-5-chloro-2-piperidinyl)-2,5-Piperazinedione

A solution of 1.5 g. of 3,6-bis(5-chloro-2-piperidinyl)-2,5piperazinedione dihydrochloride in 200 ml. of water is cooled in an ice bath and 1.0 g. of sodium nitrite is added. The cooling bath is removed and the mixture is stirred 24 hours. The precipitate is collected, 804 mg., boiled in 100 ml. of hot methanol, and filtered. The filtrate is concentrated to 50 ml. and allowed to cool. 0.52 G. of 3,6-bis-(N-nitroso-5-chloro-2-piperidinyl-2,5-piperazinedione is collected.

EXAMPLE 31

3,6-Bis-[(5-chloro-1-(2-hydroxyethyl)-2-piperidinyl]-2,5-Piperazinedione

A solution of one part 3,6-bis(5-chloro-2-piperidinyl)-2,5-piperazinedione in 250 parts of methanol is cooled in an ice bath and 10 parts of ethylene oxide are condensed into the solution. After standing 2 weeks the mixture is concentrated in vacuo to a solid which is warmed in 10 parts of methanol. After cooling 0.5 parts of product is collected. Further purification is achieved by recrystallization from methanol or by conversion to the dihydrochloride. The dihydrochloride is prepared by warming in 30 parts of methanol containing excess hydrogen chloride. After cooling, the solid is collected, washed 4 x 10 parts with methanol, and dried under vacuum.

EXAMPLE 32

3,6-Bis-[5-chloro-1-(2-chloroethyl)-2-piperidinyl]-2,5-Piperazinedione

136 Mg. of freshly prepared chloromethylenedimethylammonium chloride is dissolved in 3 ml. of dry dimethylformamide and stirred under a nitrogen atmosphere with ice-bath cooling before 205 mg. of 3,6-bis-[5-chloro-2-(2-hydroxyethyl)-2-piperidinyl]-2,5-piperazinedione is added. The cooling bath is removed and the mixture is stirred 15 hours. The solvent is removed in vacuo and the residual solid is dissolved in 2½ ml. of water and filtered. The filtrate is brought to pH 7 with 1N sodium hydroxide and the resultant precipitate is collected. Purification is achieved by chromatography on preparative silica gel thin layer plates using 10% methanol/chloroform as an eluant to give 100 mg. The dihydrochloride is prepared by slurrying one part of the free base in 100 parts of 5:1 methanol:chloroform and bubbling in hydrogen chloride. To the resultant solution is added 20 parts ether and the precipitate is collected after standing for one hour; 100 mg. of dihydrochloride with ~⅓ mole of ether as a solvate is obtained.

EXAMPLE 33

1,4-Dinitroso-3,6-Bis-(1-methyl-5-chloro-2-piperidinyl)-2,5-Piperazinedione

A 2 mmole portion of 3,6-bis(1-methyl-5-chloro-2-piperidinyl)-2,5-piperazinedione is stirred in a mixture of 10 ml. of acetic acid, 5 ml. of acetic anhydride, and 3 mmole of sodium acetate and 2.5 mmole of nitrosyl sulfuric acid is added portionwise in 5 minutes. After stirring 15 hours the acetic acid and acetic anhydride is removed in vacuo and the residue is slurried with water and brought to pH 7 with cold 1N sodium hydroxide. Purification is achieved by chromatography on silica gel tic plates.

When 3,6-bis(1-trifluoroacetyl-5-chloro-2-piperidinyl)-2,5-piperazinedione is employed in place of 3,6-bis(1-methyl-5-chloro-2-piperidinyl)-2,5-piperazinedione, there is obtained 1,4-dinitroso-3,6-bis(1-trifluoroacetyl-5-chloro-2-piperidinyl)-2,5-piperazinedione.

EXAMPLE 34

1,4-Dinitroso-3,6-Bis(5-chloro-2-piperidinyl)-2,5-Piperazinedione

A 1 mmole portion of 1,4-dinitroso-3,6-bis-(1-trifluoroacetyl-5-chloro-2-piperidinyl)-2,5-piperazinedione is stirred in a 2-phase system of 10ml. of chloroform and 10 ml. of 0.2 N sodium hydroxide with ice-bath cooling for 4 hours. The solvents are then removed in vacuo and the residue is chromatographed on silica gel tic plates to afford 1,4-dinitroso-3,6-bis-(5-chloro-2-piperdinyl)-2,5-piperazinedione.

Preparation of
3,6-Bis(5-chloro-2-piperidinyl)-2,5-Piperazinedione

A lyophilized culture of 3,6-bis(5-chloro-2-piperidinyl)-2,5-piperazinedione (Streptomyces griseoluteus NRRL 3412) is suspended in 2 ml. of a medium having the following composition:

| | |
|---|---|
| Yeast extract | 10 g. |
| Glucose | 10 g. |
| Phosphate buffer* | 20 ml. |
| MgSO$_4$.7H$_2$O | 0.5 g. |
| Distilled water | 1000 ml. |

*Phosphate buffer
| | |
|---|---|
| KH$_2$PO$_4$ | 91 g. |
| Na$_2$HPO$_4$ | 95 g. |
| | to 1000 ml. with distilled water. | and used to inoculate slants containing the same media plus 2% agar. The slants are then incubated at 28° C. for five days or until well sporulated.

To the sporulated slant is added 10 ml. of a medium having a pH of 7 to 7.2 and consisting of

| | |
|---|---|
| dextrose | 1% |
| N-Z amine | 1% |
| NaCl | 0.5% |
| meat extract | 0.3% |
| distilled water q.s. ad | | and the growth on the slant is scraped into the suspension and used to inoculate a 250 ml. baffled Erlenmeyer flask containing 50 ml. of the same medium. The inoculated flask is then placed on a rotary shaker and incubated at 28° C. for 72 hours or until good vegetative growth is obtained.

An inoculum of 10 ml. of the resulting vegetative growth is then used to inoculate a 2 L. baffled Erlenmeyer flask containing 500 ml. of sterilized medium of the same composition as shown above, and the inoculated flask is then placed on a rotary shaker and incubated for 72–96 hours at 28° C. or until good vegetative growth in obtained.

The resulting fermentation broth is used to inoculate a 50 gallon stainless steel fermentor containing 160 L. of the medium of the same composition shown above. The inoculated medium is incubated at 28° C. with agitation at 150 r.p.m. while maintaining an air flow of 3 c.f.m. through the fermentation broth. During the 72–96 hour fermentation period, small amounts of an antifoamant (Polyglycol 2,000) is added to control foaming of the batch.

8.3% of the resulting broth is then used to inoculate a 200 gallon stainless steel fermentor containing 440 L. of a medium having a pH of from 7 to 7.2 and having the following composition:

| | |
|---|---|
| Dextrose | 10.0 g./L. |
| Peptone | 5.0 g./L. |
| NaCl | 12.7 g./L. |
| Yeast extract | 3.0 g./L. |
| KCl | 0.72 g./L. |
| $FeSO_4(NH_4)_2SO_4 \cdot 6H_2O$ | 0.035 g./L. |
| $MgCl \cdot 6H_2O$ | 5.32 g./L. |
| $CaCl_2 \cdot 2H_2O$ | 0.728 g./L. |
| Distilled water q.s. ad | |

The inoculum is incubated for 120 to 160 hours with agitation at 130 r.p.m. while maintaining an air flow of 10 c.f.m. through the broth, a defoamer being added if necessary.

Filtered broth (100 gal.) obtained by the fermentation procedure described above is filtered and concentrated in vacuo to approximately 16 gallons and a 5 gallon portion of the concentrated broth is lyophilized.

1 Kg. of lyophilized filtered broth representing a lyophilized portion from a 16 gallon concentrated broth obtained above is suspended in 5 L. of absolute ethanol. The mixture is then filtered to remove insoluble material and the filtrate subsequently concentrated to an aqueous solution.

The insoluble residue from the initial ethanol extraction is extracted with 2500 ml. of absolute ethanol. The ethanol soluble fraction after filtration is concentrated in vacuo to a small volume. A crystalline fraction is observed salting out and removed by centrifugation, suspended in water and lyophilized.

A small amount of the crystalline fraction obtained is mixed with about 5 ml. water and about 10 ml. of methanol and concentrated to dryness after adding about 10 ml. of methanol two times. The final solids are then dissolved in 25–35 ml. of absolute methanol and allowed to stand at room temperature for 12 hours after which a small amount of crystalline material separated out. The sample is then cooled to 45° C. for four days and the resulting crystalline fraction is removed by centrifugation and dried in vacuo. The crystalline material thus obtained decomposed at 330° C. leaving a brown residue.

80 Mg. of crystalline sample is dissolved in N/10 hydrochloric acid, then neutralized slowly with N/10 sodium hydroxide to convert it to the free base. A precipitate forms at about pH 7. It is collected in a centrifuge tube and dried in vacuo to yield 54 mg. of 3,6-bis(5-chloro-2-piperidinyl)-2,5-piperazinedione as the free base. Analysis: Calculated for $C_{14}H_{22}N_4O_2Cl_2$; Cl, 20.3%. Found: Cl 19.07%.

The free base thus obtained is dissolved in methanol, a trace of insoluble impurity is separated and the solution is acidified by addition of alcoholic hydrogen chloride. The solvent is evaporated at reduced pressure to a small volume. On standing, white crystals of the hydrochloride form. The crystals are purified by recrystallization from methanol and dried in vacuo. No melting point is observed below 330° C. Anal. Calc. for $C_{14}H_{22}N_4O_2Cl_2 \cdot 2HCl$; C, 39.8; H, 5.74; N, 13.25; O, 7.59 Cl, 33.5. Found: C, 40,23; H, 5.85; N, 12.76; O, 8.5; Cl, 32.82.

Assay

The novel 3,6-bis(2-piperidinyl)-2,5-piperazinedione compounds of this invention may be conveniently assayed for anti-tumor activity using the Human Tumor-Egg Host System, tumor implants of human epidermoid carcinoma (H.Ep. No. 3) are placed on the chorioallantoic membranes of ten-day embryonated eggs. The eggs are incubated one day, and those showing positive "takes" are selected for the test. The 3,6-bis(2-piperidinyl)-2,5-piperazinedione compound is then injected onto the chorioallantoic membranes of the egg. Seven days after injection, the eggs are harvested and tumors and embryos from treated and untreated control groups are weighed and the percent growth inhibition of the tumor and embryo in the treated egg is obtained as follows:

Ten tumor implanted eggs are sacrificed at the time of injection with the 3,6-bis(2-piperidinyl)-2,5-piperazinedione compound to determine mean weight of the tumor. The value obtained is then subtracted from the mean weight obtained from the treated and untreated control tumors at the time of the harvest to determine the actual increase in weight of the tumors during the treatment period. The percent growth retardation for treated eggs is obtained by comparing the increase in weight of treated tumors with the increase in weight of untreated control tumors using the formula (100-T/C × 100). The percent growth retardation for embryos is determined in a similar manner.

After determining the effect of treatment on primary growth of the H. Ep. No. 3 tumor, a portion of lung tissue from each harvested embryo is implanted into a fresh group of 10-day eggs. The eggs are incubated for 8 days and then weighed the resulting tumors to obtain an estimate of the amount of metastasis to the lung.

The anti-tumor activity of the 3,6-bis(2-piperidinyl)-2,5-piperazinedione compounds of this invention employing the assay with human epidermoid carcinoma (H. Ep. No. 3) are found in Table 1.

TABLE 1

| Biological Assay in Eggs Against H. Ep. No. 3 Tumor | | | | | |
|---|---|---|---|---|---|
| Name | Dose mg/egg | Deaths | % Reduction Embryo | Tumor | Metastasis |
| 3,11-dichloro-8,16-dioxo- (2,3c:5,6c'bis octahydro [imidazo (1,5a) pyridino] hexahydropyrazine | 5 | 0/6 | 23 | 28 | 104 |
| | 1.6 | 0/6 | 6 | 1 | 95 |
| | 0.5 | 0/6 | 4 | 9 | 39 |
| 3,6-bis-[5-chloro-1-(2-hydroxyethyl)-2-piperidinyl] 2,5-piperazinedione | 1.25 | 4/6 | 37 | 96 | 101 |
| | 0.42 | 1/6 | 10 | 38 | 62 |
| | 0.14 | 3/6 | −9 | 19 | −35 |
| 3,6-bis-[1-(o-nitrophenyl-sulfenyl)-5-chloro-2-piperidinyl]-2,5-piperazinedione | 3 | 0/3 | 16 | −26 | 28 |
| | 1 | 0/3 | −8 | −5 | −47 |
| | 3 | 0/6 | −5 | −29 | 30 |
| 3,6-bis-(1-methyl-5-chloro-2-piperidinyl)-2,5-piperazinedione | 1 | 0/4 | 29 | 80 | 100 |
| | 0.33 | 0/4 | 15 | 36 | 100 |
| | 0.3 | 0/6 | 4 | 5 | 56 |
| | 0.1 | 0/6 | −11 | 30 | 28 |

TABLE 1-continued

Biological Assay in Eggs Against H. Ep. No. 3 Tumor

| Name | Dose mg/egg | Deaths | % Reduction Embryo | Tumor | Metastasis |
|---|---|---|---|---|---|
| 3,6-bis- 2-[1-azabicyclo (3,1,0)hexane] -2,5-piperazinedione | 0.09 | 1/6 | 39 | 79 | 102 |
| | 0.03 | 0/6 | 15 | 33 | 92 |
| | 0.01 | 0/6 | −2 | 25 | 77 |
| 3,6-bis[5-chloro-1-(2-chloroethyl)-2-piperidinyl]-2,5-piperazinedione | 1 | 0/6 | 42 | 86 | 99 |
| | 0.33 | 1/6 | 30 | 84 | 100 |
| | 0.11 | 1/6 | 18 | 32 | 95 |
| | .037 | 0/6 | 11 | 40 | 71 |
| | .0123 | 3/6 | 0 | 40 | 53 |
| 3,6-bis(5-hydroxy-2-piperidinyl)-2,5-piperazinedione | 3 | 0/4 | 7 | 59 | 92 |
| | 1 | 0/4 | −16 | −12 | −92 |
| | 0.33 | 0/4 | −19 | 33 | 63 |
| | 1 | 2/6 | 8 | 19 | 97 |

The anti-metastasis activity using H. Ep. No. 3 tumor cells in ova of the 3,6-bis-(2-piperidinyl)-2,5-piperazinedione compounds of this invention is compared against 3,6-bis(5-chloro-2-piperidinyl)-2,5-piperazinedione and other known anti-tumor agents, for example cyclophosphonamide, 1,3-bis(2-chloroethyl)-1-nitrosourea (BCNU) and cytosine arabinoside. Table 2 gives the activities relative to 3,6-bis(5-chloro-2-piperidinyl)-2,5-piperazinedione as 100 in this anti-metastasis assay.

TABLE 2

Anti-Metastasis Assay in Eggs Against H. Ep. No. 3 Tumor Cells

| | |
|---|---|
| 3,6-bis(5-chloro-2-piperidinyl)-2,5-piperazinedione | 100 |
| Cyclophosphonamide | Toxic |
| BCNU | 3 |
| Cytosine arabinoside | 20 |
| 3,6-bis(5-hydroxy-2-piperidinyl)-2,5-piperazinedione | <1 |
| 3,6-bis(1-methyl-5-chloro-2-piperidinyl)-2,5-piperazinedione | 10 |
| 3,6-bis[5-chloro-1-(2-hydroxyethyl)-2-piperidinyl]-2,5-piperazinedione | 2 |
| 3,6-bis[5-chloro-1-(2-chloroethyl)-2-piperidinyl]-2,5-piperazinedione | 30 |
| 3,6-bis[1-(o-nitrophenylsulfenyl)-5-chloro-2-piperdinyl]-2,5-piperazinedione | <1 |
| 3,6-bis(1-nitroso-5-chloro-2-piperdinyl)-2,5-piperazinedione | <2 |
| 3,6-bis{2-[1-azabicyclo(3,1,0)hexane]}-2,5-piperazinedione | 100–200 |
| 3,11-dichloro-8,16-dioxo-2,3c:5,6c')bis{octahydro[imidazo(1,5a)pyridino]}-hexahydropyrazine | 2 |

As indicated above, the 3,6-bis(2-piperidinyl)-2,5-piperazinedione compounds of this invention possess anti-tumor activity and are convenient reference compounds for the testing of other compounds for this activity.

What is claimed is:

1. A compound having the formula:

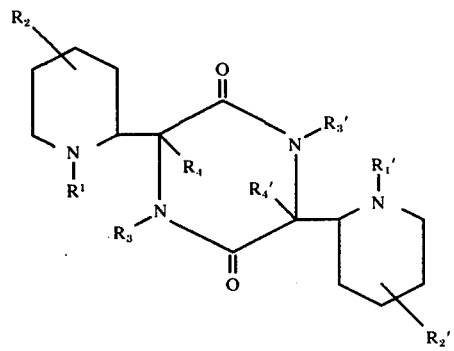

wherein $R_1$ and/or $R_1'$ is haloloweralkyl; $R_2$ and/or $R_2'$ is halogen; and $R_3$, $R_3'$, $R_4$ and $R_4'$ are hydrogen.

2. The compound of claim 1 wherein $R_1$ and $R_1'$ are haloloweralkyl, $R_2$ and $R_2'$ are chloro, and $R_3$, $R_3'$, $R_4$, $R_4'$ are hydrogen.

3. The compound of claim 2 wherein $R_1$ and $R_1'$ are 2-chloroethyl.

* * * * *